United States Patent [19]
Landis et al.

[11] Patent Number: 5,626,565
[45] Date of Patent: May 6, 1997

[54] MEDICAL TUBE HOLDER AND SUPPORT STRUCTURE

[75] Inventors: Robert M. Landis, Mountainside; Bernard Ackerman, Metuchen, both of N.J.

[73] Assignee: Ackrad Laboratories, Inc., Cranford, N.J.

[21] Appl. No.: 377,857

[22] Filed: Jan. 25, 1995

[51] Int. Cl.⁶ ............................................. A61M 5/00
[52] U.S. Cl. ...................... 604/174; 604/180; 604/179
[58] Field of Search ................ 128/DIG. 26; 604/174, 604/177, 178, 179, 180

[56] References Cited

U.S. PATENT DOCUMENTS

| | | | |
|---|---|---|---|
| 3,368,564 | 2/1968 | Selix | 604/180 |
| 3,834,380 | 9/1974 | Boyd | 604/180 |
| 3,957,082 | 5/1976 | Fuson et al. | 604/174 X |
| 4,161,677 | 7/1979 | Fuchs | 604/177 |
| 4,224,937 | 9/1980 | Gordon | 604/180 X |
| 4,250,880 | 2/1981 | Gordon | 604/180 |
| 4,769,010 | 9/1988 | Fenton, Jr. et al. | 604/180 |
| 4,838,878 | 6/1989 | Kalt et al. | 604/180 |
| 5,147,319 | 9/1992 | Ishikawa et al. | 604/174 |
| 5,419,319 | 5/1995 | Werner | 604/174 X |

*Primary Examiner*—Sam Rimell
*Attorney, Agent, or Firm*—Kenneth R. Schaefer

[57] ABSTRACT

The invention is addressed to a medical tube holder of resilient material for the placement of endotracheal, gastrointestinal or other tubes relative to the body of a patient. The preferred embodiment includes body attachment site, a medical tube support extension projecting from the body attachment site and a frictional tube engagement structure.

24 Claims, 6 Drawing Sheets

MEDICAL TUBE HOLDER AND SUPPORT STRUCTURE

BACKGROUND OF THE INVENTION

This invention relates to medical tube holders of a type which is attached to the outer surface of a patient's body.

In a number of hospital and homecare settings, the ability to securely attach one or a variety of medical tubes to the body of a patient is important in facilitating medical care. Any device which is to be used for such a purpose should satisfy a number of requirements—it should maintain the medical tube in its proper position on the patient's body despite movement by the patient; it should be convenient for the nurse or practitioner to use, allowing them to install, adjust or relocate the medical tube periodically as required, preferably without the need to adjust tape or loosen sutures; and it must be as comfortable as possible for the patient.

The simplest and most common method of attaching medical tubes to the body of a patient involves the use of adhesive tape as a means of anchoring the tube in position. The disadvantages of using adhesive tape are numerous—they include the need to apply a substantial adhesive area to the patient's skin and, at the same time, to apply the same adhesive material to the relatively small area of a slippery tube material thereby necessitating use of a potential irritant to the skin; the need for constant surveillance to monitor loss of adhesiveness; the likelihood of patient discomfort; and the increased risk of infection.

Such disadvantages have led to proposals for a number of medical tube holders of varying design. One limitation of the medical tube holders developed to date has been the degree of manual dexterity and skill required for the attachment procedure.

The Quickstrap device is an endotracheal tube holder, manufactured by IPI Medical Products of Chicago, Ill. It consists of a bite block and a non-elastic neckstrap. The neckstrap is designed so that it can be secured on a patient's head without the use of adhesive tape. The bite block is composed of a flexible, plastic-like material and fits within the neckstrap. It is the part of the device which actually holds the endotracheal tube in place. The bite block consists of two continuous regions—a U-shaped channel region, situated nearest the patient, through which the endotracheal tube is guided into the patient's mouth; and a securing region, which is essentially a notched strap with a Y-shaped rectangular metal hinge structure inserted into its middle portion.

When positioned within the Quickstrap device, the endotracheal tube lies along the longitudinal axis of the bite block. It touches the two sides of the metal hinge structure. Each side of the metal hinge structure contains five raised, rounded, abrasive metal heads in a horizontal array. Each head contacts the outer surface of the endotracheal tube when it is secured within the bite block by the tightening and securing of the strap within the neck support.

The number of potential applications of the Quickstrap device is limited in that it can only be used for placement of endotracheal tubes. In addition, its design makes it unsuitable for scaling down to the size that would be required for its use in the young child and infant patient populations. It also suffers from a number of significant other disadvantages. The neckstrap is cumbersome, covering an extensive area of the patients head and requiring considerable manipulation of the patient for its placement. The design of the neckstrap is such that it could also cause the patient a considerable degree of discomfort; the plastic straps of the bite block are difficult to secure; the use of notches of fixed position for securing the strap makes placement of the endotracheal tube difficult, especially when the circumference of the endotracheal tube does not exactly match the position of the notch. In addition, application of a force greater than that required for secure placement could be necessitated by the arrangement of the notches and could lead to undesireable constriction of the tube; the use of an elasticated strap to compress the abrasive heads of the hinge structure as a means of securing the PVC endotracheal tube leads to progressive constriction if over tightened, a result of continuing forces from the elasticated band itself, tube warming and the pliable characteristics of the PVC tube.

A medical tube holder designed for use with infants is disclosed in U.S. Pat. No. 4,906,234 issued Mar. 6, 1990 to Thomasz H. Voychehovski. The '234 patent describes a device suitable for the secure placement of a medical tube such as an endotracheal tube in an infant. The device of the '234 patent consists of a band, extending across the full width of the infant's face, which is attached by three adhesive pads to the skin. A series of receptacles positioned at regular intervals along the band are each capable of receiving an anchor element. Each anchor element, consisting of a plug and collar, is the part of the device which actually holds the medical tube securely in place. The numerous receptacles situated along the length of the band only allow medical tubes to be placed at predetermined positions and, at the same time, unecessarily complicate the device.

An endotracheal tube holder designed for use with infants is disclosed in U.S. Pat. No. 4,683,882 issued Aug. 4, 1987 to Jesse S. Laird. The device of the '882 patent consists of a base portion which is attached to the infant's face by an adhesive strap and a clamp which is supported on the base portion. The clamp can be one of three types of design—a gate-type clamp, in which the rotary movement of a thumbscrew causes a clamp member to move in a linear direction thereby locking the medical tube against the base portion; a C-clamp, in which the turn of a thumbscrew either loosens or tightens the clamp about the tube; or a clamp consisting of a strap connected to a clamp-base element. The latter type of clamp design is discussed in more detail below.

The devices of the '234 and '882 patents suffer from significant disadvantages, especially when they are used in the young child or infant patient populations. The clamp type embodiments are unsuitable for many medical applications since they require one end of the tube to be threaded through the device in order to be clamped. Such a procedure is often impossible and always undesirable. The mechanisms of using a thumb screw to clamp the tube may be hazardous when the thumb screw length-of-travel allows the user to inadvertently obstruct the flow of fluid through the tube. If a limitation on the thumb screw length-of-travel is introduced into the design in order to avoid obstruction of the tube, the device becomes tube size specific. Such size specificity would limit the device's general application and so would be an undesirable feature. In addition, external forces exerted on the tube can be transmitted to the surface of the patient's skin. The devices do not contain means of strain relief to reduce skin damage and/or tube kinking.

The device of U.S. Pat. No. 4,392,857 issued on Jul. 12, 1983 to Anthony V. Beran discloses a tube holder which includes a clamp comprising a clamp base and a wrap-around strap. At least one side of the wrap-around strap and one arm of the clamp base contain complementarily-formed triangular slots. The interlocking nature of the complementary slots situated on the clamp base and wrap-around strap act as the primary means of securing the medical tube within the tube holder.

The clamp of the '857 patent is deficient in that, even when used in an adult patient population, it requires an operator to use a high degree of manual dexterity in a movement which often leaves the medical tube free to move in an uncontrolled manner when the clamp is being engaged around it. In addition, once secured within the clamp it is difficult to disengage the medical tube. These disadvantages act to increase patient discomfort and become significant limitations on use of the clamp, especially once reduced to the scale required for use in the young child and infant patient populations.

One embodiment of the '882 patent discussed earlier, describes a clamp consisting of a strap with a notched end which is secured within a keeper element. The strap wraps around the medical tube and the notched end is placed within the keeper element. The medical tube is then secured within the clamp by pulling the strap through the keeper element until it is taut.

The clamp described in this embodiment of the '882 patent is an improvement over that described in the '857 patent in as much as it allows the medical tube to be more easily disengaged. However, the clamp of the '882 patent is rigid and requires a strong gripping action and significant manual dexterity on the part of the operator. Moreover, another significant disadvantage shared by both clamps arises from the use of notches of fixed position as the primary means of securing a medical tube. As discussed earlier with use of the Quickstrap device, none of the fixed positions may correspond exactly to the diameter of a specific medical tube thus necessitating the application of force by the operator and ultimately constriction of the medical tube in order to obtain its secure placement within the clamp. The application of force, especially by those unskilled in using the device, may lead to patient discomfort and movement of the medical tube within the patient's body. More seriously, the constriction of the medical tube may, in some instances, be dangerous to the patient's health and general well being. The '882 patent does not describe any means of strain relief between the point where the tube is clamped and its point if contact with the patient's skin.

In today's healthcare climate with its emphasis on homecare and other alternatives to prolonged hospitalization, the availability of a simple, effective means of securing a medical tube to a patient's body which is capable of being readily utilized by the skilled and unskilled alike, is highly desirable.

The present invention contemplates provision of an inexpensive, easy to apply means of securing a medical tube to a patient's body. The manner in which this has been achieved is by the design of a clamp which secures a medical tube by means of a wrap-around non-elastic strap. Due to its unitary construction and the simplicity associated with its use, the present invention is particularly suited to applications involving young children and infants aswell as to those applications where medical tubing needs to be safely secured while still allowing easy release and re-securing for body depth tube adjustments.

SUMMARY OF THE INVENTION

The present invention achieves its objectives in a simple, straightforward, yet elegant manner. The medical tube holder is of unitary construction composed of a resilient plastic material such as polypropylene. The physical properties of such materials impart structural strength and rigidity to the holder while their availability combined with ease of use makes manufacture of the holder economical.

The body attachment site, that portion of the holder which contacts the body of the patient and provides a means of securely fixing the device to the patient's body, can be constructed in a number of ways. For example, in one embodiment of the holder, the body attachment site consists of a generally rectangular, anatomically curved flange. For patient safety and comfort, a pad of foam-like material is bonded to the innermost surface of the body attachment site of this embodiment. Surgical or other adhesive-type tape can be attached in a variety of configurations in order to provide a stable and secure anchoring site for the holder.

Alternatively, in a separate embodiment, the body attachment site consists of a generally rectangular pad of foam-like material to which the holder is attached via at least two flange members. The underside of the foam pad of this embodiment can be coated with an adhesive preparation which is compatible with human skin, thereby providing a means by which the holder can be securely attached to the body of a patient independent of surgical or other types of adhesive tape.

The medical tube support extension, that portion of the holder which provides a means of attachment and support for the medical tube, is continuous with the body attachment site and, in the first embodiment of the holder, described above, preferably extends from the central portion of one side of the rectangular curved flange. The support extension is of unitary construction and is preferably composed of two functional regions.

The support structures in both embodiments described above contain the same functional regions. The first region of the support structure, the stress dissipation region, is designed so that it can easily flex or bend. Its malleability dissipates the stress forces exerted on the body attachment site by movement of the medical tube. It thus imparts an added degree of stability to the placement of the medical tube and decreases the risk of patient discomfort. In addition, by reducing the overall amount of force exerted on the medical tube, the stress dissipation region minimizes the possibility that the tube will become constricted or otherwise contorted.

The second functional region of the support extension is the medical tube securing region. The securing region preferably contains a centrally located concave (e.g. semicircular) trough which runs along at least part of its entire length. Two projections of equal size extend upward from one side of the securing region forming an angle such as 90° with the securing region. These projections form a lateral motion inhibitor complex which prevents lateral movement of the medical tube once it is secured within the holder.

An elongated, non-elastic, flexible fabric securing strip can be attached by means of a frictional metal clip situated within that portion of the central trough of the securing region of the support extension lying at the end of the holder opposite the body attachment site. The securing strip, which is preferably composed of soft and pliable material, can be of variable length depending on the diameter of medical tube it is required to enclose. The inner surface of the securing strip is composed of a dense pile of nylon fiber loops. On the lower surface of the securing region of the support extension, attached by means of the same frictional metal clip which holds the securing strip, is a strip of fabric, the outer surface of which is composed of a dense arrangement of nylon hooks. The firm bond formed when the nylon fiber loops on the securing strip contact the nylon hooks on the lower fabric strip comprise the primary means of securing the medical tube in position once it is placed within the holder. In order to further facilitate the secure placement of the medical tube within the holder, the securing strip has at least two additional frictional metal clips located along its length. The abrasive metal clips are situated such that their rounded, raised, abrasive heads contact the outer surface of the medical tube once it is placed within the holder.

It is an object of the present invention to provide a medical tube holder to accommodate medical tubes of varying diameters which is both inexpensive to manufacture and simple in its method of use.

It is another object of the present invention to provide a medical tube holder which is capable of securely immobilizing a medical tube with only the application of a minimum amount of force, so as to avoid the potential for constriction of the medical tube.

It is another object of the present invention to provide a medical tube holder with a securing strap that is non-elastic in order to avoid the potential for constriction of the medical tube by the foces of retraction which may be exerted over time.

It is another object of the present invention to provide a medical tube holder consisting of a securing strap that is composed of a soft and pliable material in conjunction with attached rigid members to securely contact the tube.

It is another object of the present invention to provide a medical tube holder which provides flex and strain relief between the point where the device contacts the patient's skin and the point where it is secured.

It is another object of the present invention to provide a medical tube holder of a design which enables an operator to place a medical tube within the holder from a lateral position thus obviating the need to remove connections or thread the medical tube from one end for placement.

It is another object of the present invention to provide a medical tube holder of a design which allows it to be manufactured in a variety of different sizes such that it is easily adaptable to use in all types of patient populations.

These and other objects of the present invention will become more apparent to those skilled in the art from the following description of the invention taken in conjunction with the accompanying drawings.

DESCRIPTION OF PREFERRED EMBODIMENTS OF THE INVENTION

Preferred embodiments of the invention incorporate a number of features. The specific form of those features presented in the preferred embodiment of the invention is in accordance with its use with an endotracheal, nasal/oral, or similar tube. These applications have been selected because of their importance. In other applications other specific forms may be preferable.

Reference will now be made to the drawings, wherein like parts are designated by like numerals. A holder 10 in accordance with the present invention is a device of unitary construction. In one embodiment, shown in FIGS. 1(a) and 1(b), the holder 10 comprises an anatomically curved, generally rectangular flange 11 at an innermost end. Extending from an upper side of a central portion of, and perpendicular to the curved flange 11, is a medical tube support extension 12. The support extension 12 consists of two functional regions, a stress dissipation region 13 and a medical tube securing region 14. The medical tube securing region 14 contains a concave central trough 15 (e.g. semicircular in shape) which runs along part of its length. Once in position within the holder 10, a medical tube 16 makes contact with several portions 17, 18, 19 of the central trough 15 disposed along part of its length.

Figure 1A:
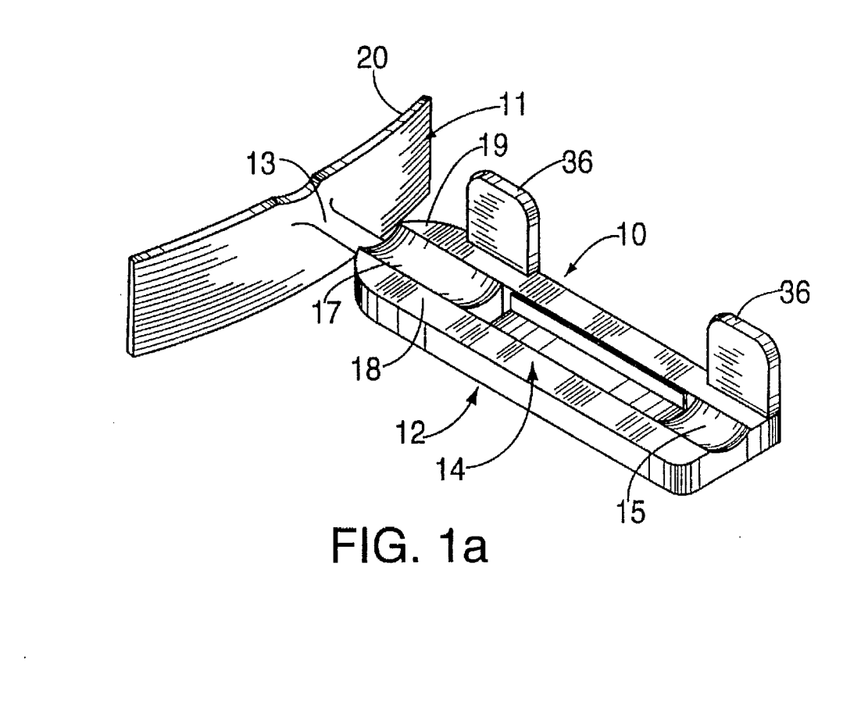
FIG. 1(a) is a perspective view of one emodiment of the device in accordance with the present invention.
Figure 1B:
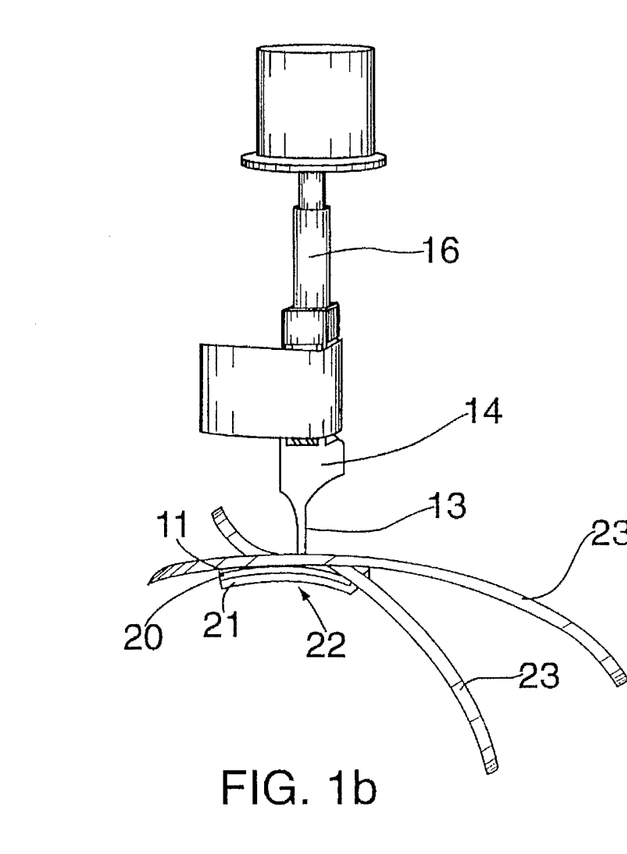
FIG. 1(b) is a perspective view illustrating the medical tube holder of FIG. 1(a) and a portion of a medical tube mounted a functional position.

Firmly bonded to, and covering the innermost surface 20 of the curved flange 11, is a pad 21 composed of a resilient, foam-like material. The curved flange 11 and the pad 21 of foam-like material together comprise a body attachment site 22. Surgical or other forms of adhesive-type tape 23 may be used to attach the holder 10 to the patient's body at the body attachment site 22 by running a strip of such tape 23 across the flange 11 which extends laterally on each side to contact the face of the patient.

Figure 2A:
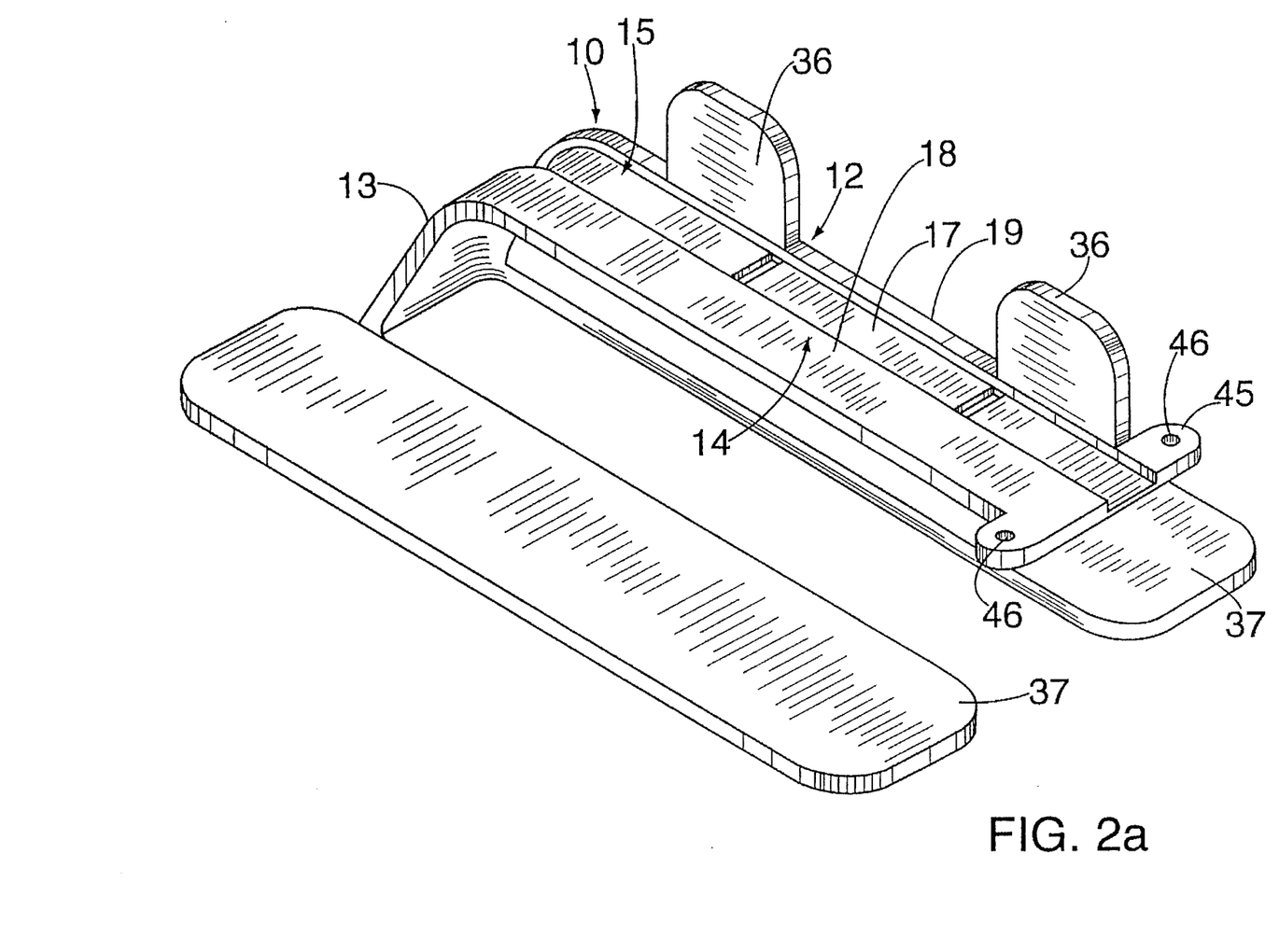
FIG. 2(a) is a perspective view of another embodiment of the device of in accordance with the present invention.
Figure 2B:
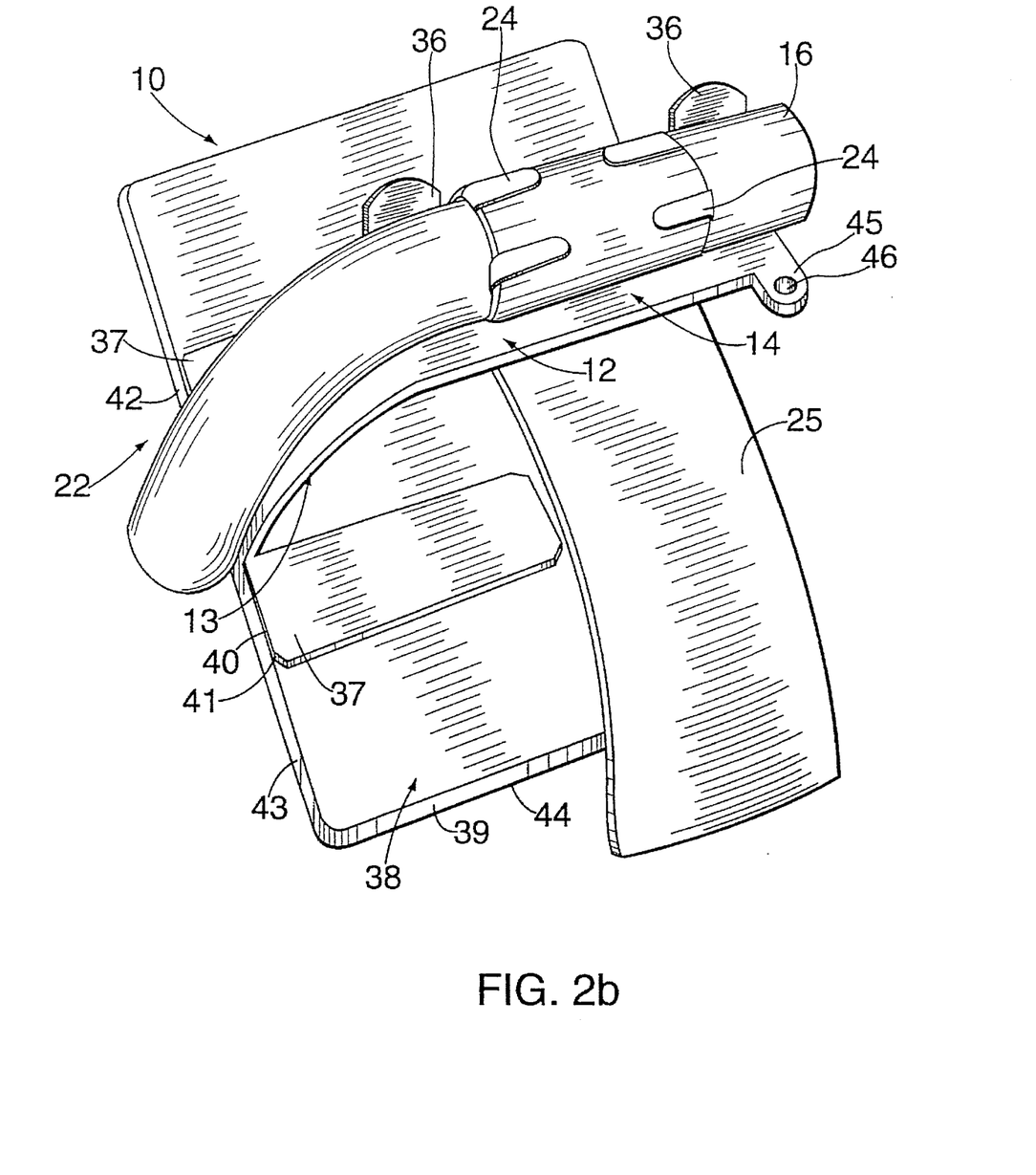
FIG. 2(b) is a perspective view illustrating the medical tube holder of FIG. 2(a) and a portion of a medical tube mounted in a functional position.

In another embodiment of the invention, shown in FIGS. 2(a) and 2(b), the medical tube holder 10 comprises two generally rectangular flange members 37 at an innermost end. Continuous with the innermost edge of each flange member and extending upwardly in a curved manner from between the two flange members 37 at an angle of less than 90° with respect to the two flange members 37 is the tube support extension 12. The tube support extension 12 extends over and runs parallel to the flange members 37. The tube support extension 12 consists of two functional regions, a curved stress dissipation region 13 and a flattened medical tube securing region 14. The medical tube securing region 14 contains a concave central trough 15 (e.g. semicircular in shape) which runs along a portion of its length. Once in position within the holder 10, a medical tube 16 makes contact with several portions 17, 18, 19 of the central trough 15 disposed along a portion of the length of the tube securing region 14.

The lower surfaces of each of the two flange members 37 are bonded to the upper surface 38 of a substantially rectangular pad of foam-like material 39. The edge 40 of the width-defining side 41 of each flange member 37 which is continuous with the medical support extension 12 lies along the edge 42 of one of the longest sides 43 of the rectangular pad of foam-like material 39.

The two flange members 37 and the rectangular pad of foam-like material 39 together comprise the body attachment site 22. The lower surface 44 of the pad of foam-like material 39 is coated with a layer of adhesive suitable for contact with human skin.

The extreme end of the tube securing means 14 contains a suture securing and safety means 45. The suture securing and safety means 45 lies perpendicular to the longitudinal axis of the tube securing means 14 and provides an added safety feature to the device. The width of the suture securing and safety means 45 is greater than that of the tube securing means 14. Each of its protruding sides contains one substantially rounded hole 46 capable of receiving suture thread. The suture securing and safety means 45 allows a practitioner to fasten a suture around the medical tube 16 thereby ensuring that the position of the medical tube 16 cannot be disturbed without the knowledge of the practitioner.

Figure 3:
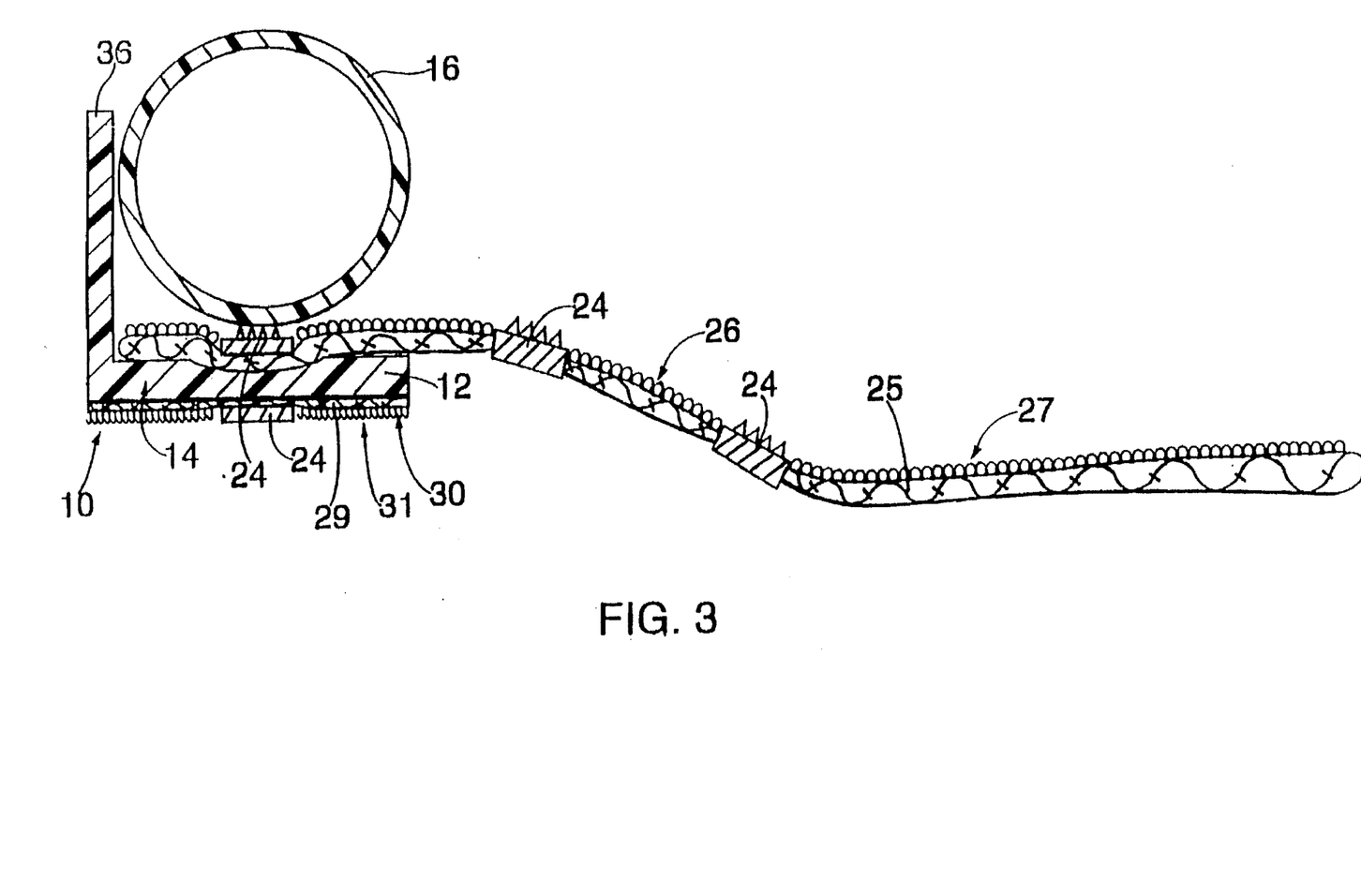
FIG. 3 is a cross sectional view of the device of the present invention with a medical tube in place but not secured.

FIG. 3 is a cross sectional view of the medical tube holder 10 in the open position with a medical tube 16 in place. Situated on the uppermost surface of the tube securing region 14 of the support extension 12, at the end opposite the curved flange 11, and attached by means of a frictional metal clip 24 is a flexible non-elastic fabric securing strip 25. An inner surface 26 of the securing strip 25 is composed of a dense pile of nylon fiber loops 27. The securing strip 25 is attached to the tube securing region 14 of the support extension 12 by means of the frictional metal clip 24 and extends outward at right angles to the support extension 12 to form a loop 28 (see FIG. 4) around the medical tube 16 once it is in place in the trough 15. The securing strip 25 can be of sufficient length to accommodate medical tubes 16 of different diameters. The securing strip 25 is attached to a securing strip attachment site 29 located on a lower surface of the tube securing region 14 of the support extension 12. An outermost surface 30 of the securing strip attachment site 29 on the lower surface of the support extension 12 is composed of a dense arrangement of nylon hooks 31. The securing strip attachment site 29 is attached to the lower surface of the tube securing region of the support extension 12 by the same frictional metal clip 24 which attaches the securing strip 25 to the upper surface of the tube securing region 14 of the support extension 12. Whenever a medical tube 16 is secured within the holder 10 as in FIG. 4, the loop portion 28 is arranged to extend over more than 180° of the surface of medical tube 16 and holds the medical tube 16 against upwardly extending projections 36 on support extension 12 as will appear below. The attachment of the dense pile of nylon fiber loops 27 of the securing strip 25 to the nylon hooks of the securing strip attachment site 29 located on the lower surface of the tube securing region 14 of the support extension 12 provides a strong bond such that the medical tube 16 is held firmly in place.

Figure 4:
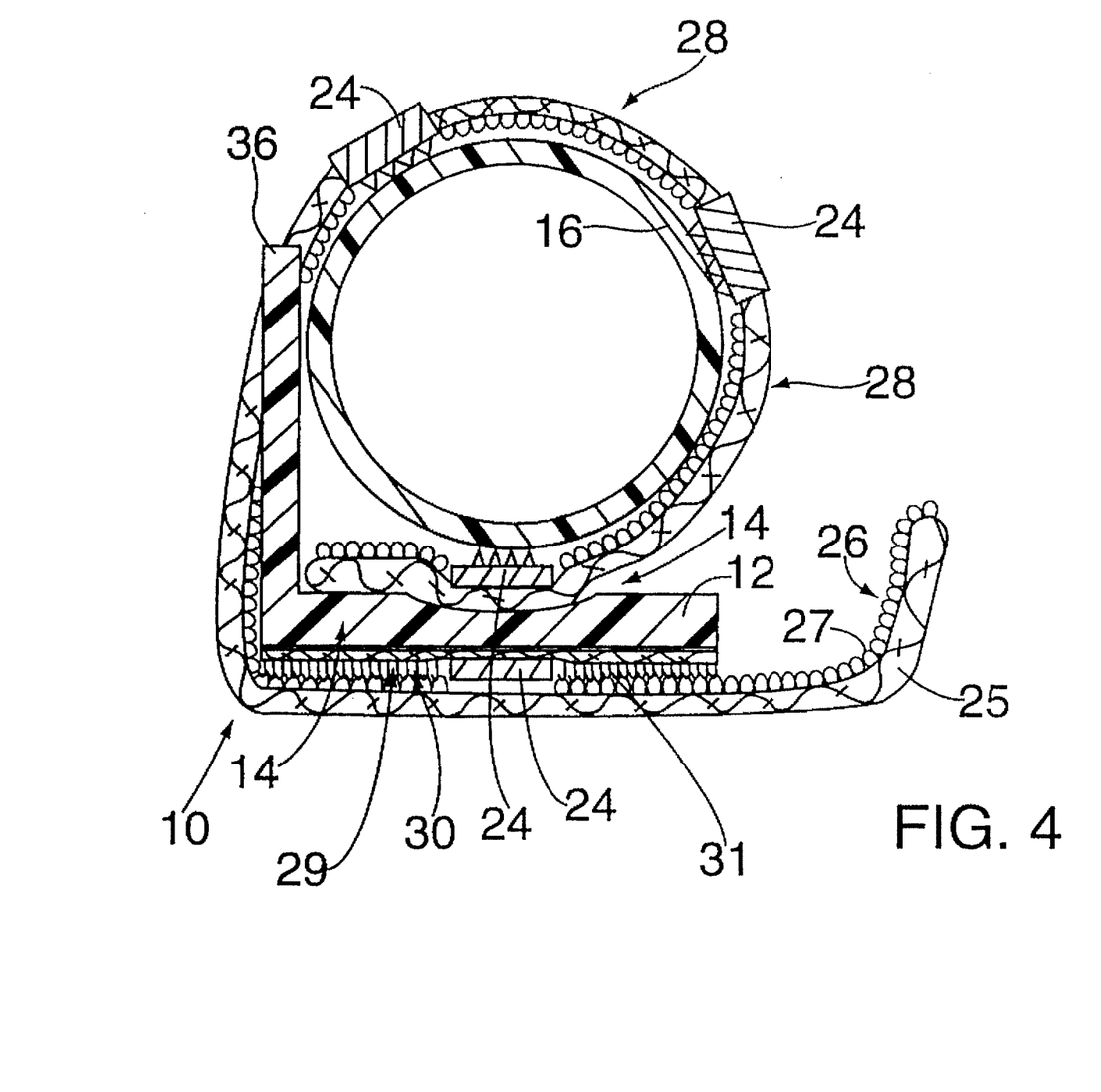
FIG. 4 is a cross sectional view of the device of the present invention with a medical tube in place and secured.

In order to enhance the secure placement of the medical tube 16 within the device 10, the securing strip 25 has at least two frictional metal clips 24 situated along its length.

Figure 5A:
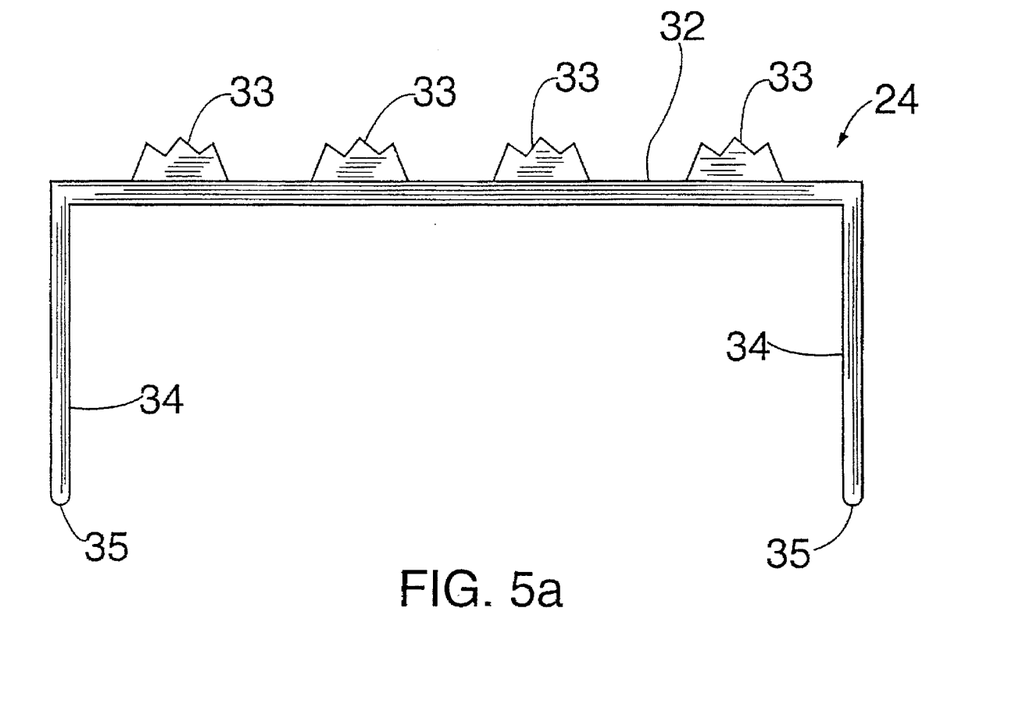
FIG. 5(a) is a perspective view of a frictional metal clip of the device of the present invention.
Figure 5B:
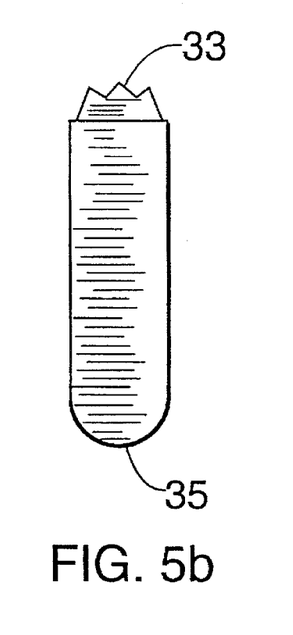
FIG. 5(b) is a side view of a frictional metal clip of the device of the present invention.

As shown in FIG. 5(a), the frictional metal clips 24 consist of a top portion 32 which contains, for example, four or more substantially round holes 33 that are raised relative to the surface. At either side, continuous with the top portion 32, and extending downwards are two leg extensions 34. The bottom of each leg 34 is fashioned such that it forms a rounded end 35 as shown in FIG. 5(b). The rounded end portions 35 of the frictional metal clip 24 penetrate the resilient material of the medical tube holder 10 at predetermined positions. Folding of the legs 34 inward provides a secure and permanent means of attaching the frictional metal clip 24 to both the tube securing region 14 of the support extension 12, the securing strip 25 and the securing strip attachment site 29. The top portion 32 of each of the frictional metal clips 24 is situated such that the raised projections 33 contact the outer surface of the medical tube 16 once it is secured in the holder 10. The outermost frictional metal clip 24 is situated on the securing strip 25 such that it contacts the circumference of the medical tube 16 at an angle of greater than 180° relative to the tube securing region 13 of the support extension 12, thereby ensuring added security to the placement of the medical tube 16.

As shown in FIGS. 1 and 2, continuous with the upper surface of the securing region 14 of the support extension 12 and situated at either end of the frictional metal clip 24 which attaches the flexible fabric securing strip 25 to the tube securing region 14 of the support extension 12, are two projections 36. The projections 36 extend upwards from the side of the tube securing region 14 of the support extension 12 at an angle of 90°. The projections 36 form a lateral motion inhibitor complex and prevent lateral movement of the medical tube 16 as the loop 28 is drawn over the circumference of the medical tube 16 to facilitate captivation of medical tube 16. The loop 28 readily may be disengaged by rotational motion with one hand, thereby leaving the other hand free to position the medical tube 16 or to do other functions as needed.

While the invention has been described in terms of a preferred embodiment, various modifications within the scope of the invention readily may occur to persons skilled in the art upon reading the foregoing specifications, which modifications are intended to be covered by the following claims.

What is claimed is:

1. A medical tube holder of resilient material for the placement of endotracheal, gastrointestinal and other such tubes relative to a patient's body comprising:
 a body attachment site compatible with contact with human flesh;
 a medical tube support extension projecting from said body attachment site, said extension comprising at least two regions; a first of said regions being a stress dissipation region having means for reduction of stress forces exerted on said medical tube holder; and a second of said regions being a medical tube support region having a concave trough running along at least a portion of its length;
 frictional tube engaging means associated with said tube support extension for inhibiting longitudinal motion of an inserted tube pressed against said engaging means; and
 means for securing a medical tube within said holder.

2. A medical tube holder of claim 1 wherein said body attachment site comprises an anatomically curved flange member.

3. A medical tube holder of claim 1 wherein said body attachment site comprises a pad of pliable material containing adhesive means on its outermost surface which is capable of conforming to the contours of a human body.

4. A medical tube holder of claim 1 wherein said means for securing a medical tube comprises an elongated flexible strip with a resilient inner surface attached, by means of a frictional metal clip, to said support extension at an end opposite said body attachment site, said means for securing further comprising an outer surface overlying a lower side of said support extension and adapted for variable tension fastening engagement with said inner surface.

5. A medical tube holder of claim 1 wherein said holder contains means whereby a medical tube can be further secured by suture or similar type thread.

6. A medical tube holder of claim 1 wherein said frictional tube engaging means comprises at least one frictional metal clip which consists of abrasive material on its upper surface and fastening legs extending downwards from each side of the upper surface and engageable with said tube support extension.

7. A medical tube holder of claim 1 wherein said medical tube support extension projects from said body attachment site, said extension having a stress dissipation region extending from the central portion of said body attachment site and a tube support region having a concave trough running centrally along at least part of its entire length.

8. A medical tube holder of claim 1 wherein said stress dissipation region extends from the central portion of said body attachment site and consists of a thin narrow strip of the resilient material of said medical tube holder which is capable of absorbing and reducing stress and other forces exerted on said medical tube and said medical tube holder.

9. A medical tube holder of claim 1 wherein said medical tube support extension contains lateral motion inhibitor means situated on one side of said support extension for inhibiting movement laterally in one direction of a medical tube inserted in said support extension comprising at least two projections which extend upwards from said medical tube support extension at an angle of not greater than 90°.

10. A medical tube holder of claim 1 wherein said means for securing a medical tube within said holder comprises one or more of:

a bond formed between the inner surface of said elongated flexible strip attached to the upper surface of said support extension and a fastening means located on the lower surface of said support extension;

contact between the outer surface of said medical tube and abrasive surfaces of a plurality of frictional metal clips situated along the length of said elongated flexible strip such that the outermost of said frictional metal clips forms an angle of greater than 180° with said frictional metal clip which attaches said elongated flexible strip to said support extension; and a lateral motion inhibitor means comprising at least two projections which extend upwards at an angle of not greater than 90° from the side of said support extension.

11. A medical tube holder of claim 1 wherein said body attachment site comprises adhesive tape extending from said body attachment site onto the surface of a patient's body.

12. A medical tube holder of claim 1 being adapted to provide for the placement of endotracheal, gastrointestinal and other such tubes relative to a patient's body wherein said patient is an infant.

13. A medical tube holder of claim 1 being adapted to provide for the placement of endotracheal, gastrointestinal and other such tubes relative to a patient's body wherein said patient is an adult.

14. A medical tube holder of claim 1 being adapted for inclusion together with medical tubes having defined length and different diameters and an elongated flexible strip with attached frictional metal clips of sufficient length to enclose said medical tubes and maintain an angle of 180° between the outermost of said frictional metal clips situated on said elongated flexible strip and said frictional metal clip which attaches said elongated flexible strip to said support extension.

15. A medical tube holder of claim 1 wherein said means for securing a medical tube within said holder is adapted for wrap-around contact with at least one-half the circumference of a medical tube.

16. A medical tube holder of claim 1 wherein said means for securing a medical tube within said holder is composed of a fabric material whose inner surface contains a pile of nylon loop fibers capable of reversibly contacting an attachment site located on the lower surface of said support extension, said attachment site containing an arrangement of nylon hooks on its outer surface allowing for secure, nonconstrictive placement of medical tubes of interchangeable diameter.

17. A method of holding a medical tube having one end thereof inserted into a patient's body, utilizing the following steps:

attaching to the surface of a patient's body, a medical tube holder comprising a body attachment site and, projecting therefrom, a medical tube support extension;

positioning said medical tube within said patient's body;

placing a medical tube on the upper surface of said support extension such that the outside surface of said medical tube contacts the inside of a concave trough which runs along a portion of said support extension; and wrapping an elongated flexible strip attached to said support extension around the circumference of said medical tube by means of a one-handed motion such that the inner surface of said elongated flexible strip contacts a fastening means located on the lower surface of said support extension.

18. The method of claim 17 wherein said elongated flexible strip is made of fabric.

19. The method of claim 17 wherein said support extension contains a means of dissipating forces exerted on said medical tube and said medical device holder.

20. The method of claim 17 wherein said elongated flexible strip is made of fabric having a pile of nylon loop fibers on its inner surface which reversibly contact an arrangement of nylon hooks located on the outer surface of a attachment site on the lower surface of said support extension.

21. The method of claim 17 wherein said step of positioning said medical tube within said patient's body being adapted for placing said medical tube in a position which is not limited by the contours of said medical tube holder.

22. The method of claim 17 wherein a plurality of frictional metal clips having an abrasive surface are attached to said elongated flexible strip along said elongated flexible strip's greatest dimension, the innermost of said plurality of frictional metal clips attaching said elongated flexible strip to said support extension, said abrasive surface of said plurality of frictional metal clips contacting the outer surface of said medical tube and forming an angle of greater than 180° with the outermost of said plurality of frictional metal clips.

23. The method of claim 17 wherein said medical tube holder is attached to the surface of said patient's body by connecting adhesive tape from said body attachment site to the surface of said patient's body.

24. The method of claim 17 wherein said medical tube holder is attached to the surface of said patient's body by forming a bond between said medical tube holder and a pad of pliable material, containing adhesive means on its outermost surface, which is capable of conforming to the contours of said patient's body.

* * * * *